(12) United States Patent
Walkington

(10) Patent No.: US 12,082,826 B2
(45) Date of Patent: Sep. 10, 2024

(54) SURGICAL COMPONENT CONNECTING DEVICE, KIT, AND METHODS OF USE

(71) Applicant: DEPUY IRELAND UNLIMITED COMPANY, Ringaskiddy (GB)

(72) Inventor: Mathew Walkington, Elland (GB)

(73) Assignee: DEPUY IRELAND UNLIMITED COMPANY, LOUGHBEG INDUSTRIAL ESTATE, Ringaskiddy (IE)

( * ) Notice: Subject to any disclaimer, the term of this patent is extended or adjusted under 35 U.S.C. 154(b) by 291 days.

(21) Appl. No.: 17/695,139

(22) Filed: Mar. 15, 2022

(65) Prior Publication Data

US 2022/0304703 A1    Sep. 29, 2022

(51) Int. Cl.
*A61B 17/16*    (2006.01)
*B23B 31/11*    (2006.01)

(52) U.S. Cl.
CPC ........ *A61B 17/162* (2013.01); *A61B 17/1631* (2013.01); *B23B 31/11* (2013.01)

(58) Field of Classification Search
CPC ... A61B 17/16; A61B 17/1613; A61B 17/162; B23B 31/11; B23B 31/1107; B23B 31/1115; B23B 31/1122
See application file for complete search history.

(56) References Cited

U.S. PATENT DOCUMENTS

| | | | | |
|---|---|---|---|---|
| 5,466,101 A | * | 11/1995 | Meyen | B25D 17/088 408/226 |
| 5,601,560 A | * | 2/1997 | Del Rio | A61B 17/162 408/231 |
| 5,741,263 A | * | 4/1998 | Umber | A61C 1/18 279/75 |
| 5,893,851 A | * | 4/1999 | Umber | A61B 17/162 279/75 |
| 6,033,408 A | * | 3/2000 | Gage | A61B 17/1633 173/218 |
| 6,325,393 B1 | * | 12/2001 | Chen | B25B 23/0057 279/22 |
| 7,448,302 B2 | * | 11/2008 | Huang | B25B 23/0035 81/177.85 |

(Continued)

FOREIGN PATENT DOCUMENTS

EP    1074225 A1    2/2001
JP    2023517989 A  *  4/2023

(Continued)

OTHER PUBLICATIONS

Search Report From Corresponding GB Application No. GB2104353.4, Dated Dec. 15, 2021, 1 Page.

*Primary Examiner* — Eric S Gibson

(57)    ABSTRACT

A surgical component connecting device, kit, and method are disclosed. The surgical component connective device includes an outer body, a body element, and a support element. The support element is slidably mounted relative to the body element. Two or more surgical component engaging elements provided towards the distal end of the body element, and at least one of the surgical component engaging elements is operably connected to the support element. The two or more surgical component engaging elements have a first state and a second state. The separation of the two or more surgical component engaging elements is greater in the second state than in the first state.

20 Claims, 3 Drawing Sheets

(56) References Cited

U.S. PATENT DOCUMENTS

| | | | |
|---|---|---|---|
| 7,740,249 B1 * | 6/2010 | Gao | B23B 31/1071 279/22 |
| 8,801,713 B2 * | 8/2014 | del Rio | A61B 17/1617 279/78 |
| 8,985,593 B1 * | 3/2015 | Gao | B25G 3/12 279/74 |
| 9,113,917 B2 * | 8/2015 | del Rio | A61B 17/1617 |
| 9,381,023 B2 * | 7/2016 | del Rio | A61B 17/162 |
| 9,681,879 B2 * | 6/2017 | del Rio | A61B 17/162 |
| 10,343,266 B2 * | 7/2019 | Zimmermann | B25B 21/00 |
| 10,456,207 B2 * | 10/2019 | Flatt | A61B 34/30 |
| 10,702,284 B2 * | 7/2020 | Högerle | B25B 23/141 |
| 10,987,112 B2 * | 4/2021 | del Rio | A61B 17/32002 |
| 11,202,642 B2 * | 12/2021 | Flatt | F16D 1/087 |
| 11,253,330 B2 * | 2/2022 | Flatt | A61B 17/162 |
| 11,723,672 B2 * | 8/2023 | Sweitzer | A61B 17/162 606/80 |
| 11,826,058 B2 * | 11/2023 | del Rio | A61B 17/32002 |
| 2005/0038443 A1 | 2/2005 | Hedley et al. | |
| 2006/0049587 A1 * | 3/2006 | Cornwell | B25B 23/0035 279/75 |
| 2009/0261536 A1 * | 10/2009 | Beale | B23B 31/1071 279/19.7 |
| 2012/0259337 A1 * | 10/2012 | del Rio | A61B 17/1617 29/428 |
| 2018/0110572 A1 * | 4/2018 | Flatt | A61B 34/70 |
| 2020/0030045 A1 * | 1/2020 | Flatt | A61B 90/98 |
| 2020/0093555 A1 * | 3/2020 | Flatt | A61B 34/30 |
| 2021/0290253 A1 * | 9/2021 | Sweitzer | A61B 17/1633 |
| 2022/0079604 A1 * | 3/2022 | Flatt | A61B 17/1624 |
| 2022/0304703 A1 * | 9/2022 | Walkington | A61B 17/1631 |

FOREIGN PATENT DOCUMENTS

| | | | |
|---|---|---|---|
| WO | 20090039346 A1 | 3/2009 | |
| WO | WO-2012138338 A1 * | 10/2012 | A61B 17/16 |
| WO | 20200224919 A1 | 11/2020 | |
| WO | WO-2021188422 A1 * | 9/2021 | A61B 17/162 |

* cited by examiner

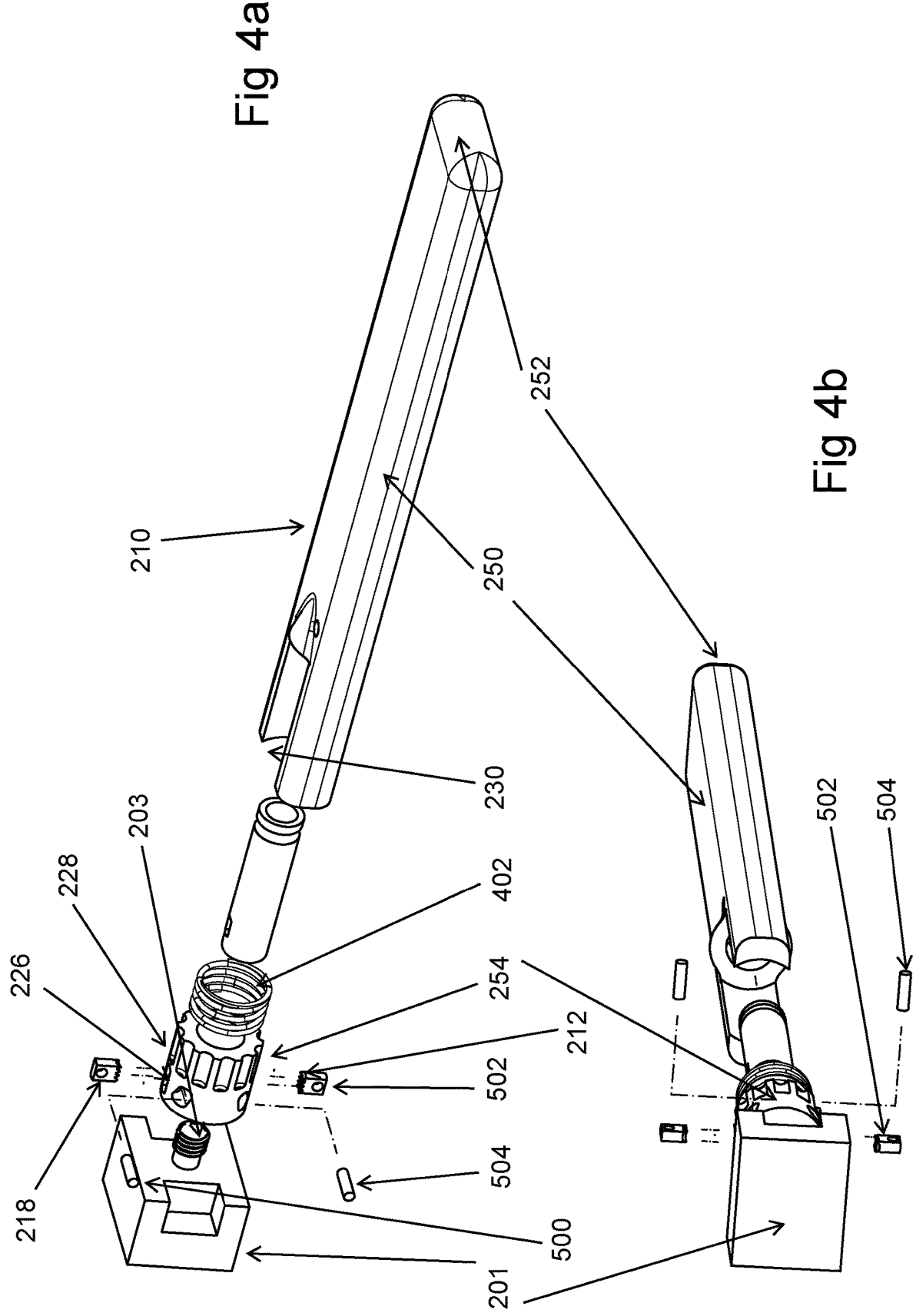

SURGICAL COMPONENT CONNECTING DEVICE, KIT, AND METHODS OF USE

The present application claims priority to UK Patent Application No. 2104353.4 which was filed on Mar. 26, 2021 and is incorporated in its entirety by reference herein.

TECHNICAL FIELD

This disclosure concerns improvements in and relating to connections, particularly, but not exclusively, in relation to a surgical component release mechanism.

BACKGROUND

It is known to provide one part of a male and female thread combination on a surgical component and to provide the other part on a connecting element. The connecting element is engaged with the surgical component by screwing the threads into engagement. A firm and resilient connection between the two is provided. When release is desired, the connecting element is rotated to unscrew the threads from engagement.

Providing and/or releasing an engagement in this and other existing approaches is time consuming to achieve. A large number of such connections may have to be made and then released. Surgical procedures generally benefit from being conducted over as short a time as reasonable.

The present disclosure may provide improvements in the ease and/or speed with which connections can be made and, particularly but not exclusively, can be released. The present disclosure may provide for the connection still to be in a resilient and reliable form. The present disclosure may provide improvements in providing release for a connection where the release is triggered remotely.

SUMMARY

According to a first aspect of the disclosure, there is provided a surgical component connecting device, the connecting device comprising:
  an outer body;
  a body element;
  a support element, the support element being slidably mounted relative to the body element; and
  two or more surgical component engaging elements provided towards the distal end of the body element, at least one of the surgical component engaging elements being operably connected to the support element;
    wherein the two or more surgical component engaging elements have a first state and a second state, wherein the separation of the two or more surgical component engaging elements is greater in the second state than in the first state.

The outer body may have a proximal end and a distal end. The proximal end may include one or more openings, for instance to allow access to a part of the body element, preferably a handle section of the body element. The outer body may be provided with one or more operator contacting sections, preferably at or towards the proximal end of the outer body. The outer body may be elongate. The outer body may be provided with an outer body bore at the distal end. The outer body bore may extend the length of the outer body.

The body element may be rotatably mounted relative to the outer body. The body element may be rotatably mounted on the inside of the outer body. The body element may be a shaft, preferably a hollow shaft. The body element may have a proximal end and a distal end. The proximal end may provide a handle section. The distal end may provide a connection location for the surgical component. The body element may be elongate. The body element may have a longitudinal axis extending from the distal end to the proximal end. The body element may be provided with a bore at the distal end. Preferably the connection location is provided within the bore. The body element may define a surface at the distal end, preferably perpendicular to the axis of the body element.

The support element may be slidably mounted on the outside of the body element. The support element may be an annular element. The support element may extend at least partially around the body element, for instance having an annular extend of greater than 190°.

In the first state the support element may be closer to the distal end of the body element than in the second state. During transition from the first state towards the second state, the support element may slide towards the proximal end of the body element.

The support element may be acted on by a biasing unit. The biasing unit may bias the support element towards the distal end of the body element. The biasing unit may bias the support element towards the first state position. The biasing unit may resist the support element moving towards the proximal end of the body element. The biasing unit may resist the support element moving away from the first state position towards the second state position. The biasing unit may be connected to the body element. The biasing unit may be mounted on the body element. The biasing unit may be a spring or a deformable component. The biasing unit may be deformed during transition away from the first state towards the second state.

Particularly in the first state, a distal end of the support element may be aligned with the distal end of the body element. The support element may define a support element surface at the distal end, preferably perpendicular to the axis of the body element. The support element surface and the body element surface may be coplanar. One or both of the surfaces may abut the surgical component when the surgical component is connected to the connecting device.

The support element may be slidably mounted on the body element and restrained from rotation relative to the body element. The body element may be provided with a guiding slot. The body element, support element and engaging elements may be rotationally restrained relative to one another, but preferably are not rotationally restrained relative to an outer body. Rotation of the body element may cause rotation of the support element and rotation of the engaging elements, but preferably does not cause rotation of an outer body. The guiding slot may cooperate with a part connected to the support element to restrain rotation of the support element. The part may extend through the guiding slot from the inside to the outside of the body element. The part may be connected to an engaging element or may be an engaging element. Preferably a guiding slot is provided for each engaging element and/or each engaging element is connected to a part.

The part may be slidably connected to the support element. The part may be slidably connected to a rib provided on the support element, preferably extending inward from the support element. The rib may be provided to one side of the guiding slot.

The two or more surgical component engaging elements may oppose one another. The engaging elements may be regularly spaced, in an angular sense. For instance two engaging elements may be provided at an angular separation of 180° to one another +/−10°. For instance, three engaging elements may be provided at an angular separation of 120° to one another +/−20°.

One or more or all of the engaging elements may be provided with a surgical component engaging surface, preferably provided on the innermost edge of the engaging elements. One or more or each engaging surface may be provided with a threaded portion, preferably a female threaded portion.

One or more or all of the engaging elements may each be slidably mounted relative to the support element. One or more or all of the engaging elements, preferably each, is operably connected to the support element. One or more or all of the engaging elements may extend radially, for instance away from their engaging surface. One or more or all of the engaging elements may extend through its guiding slot in the body element.

Preferably one or more or all of the engaging elements are directly mounted to the support element, but with a slidably mounted. Alternatively, one or more or all of the engaging elements may be indirectly mounted to the support element, but with a slidably mounted relative thereto.

One or more or all of the engaging elements preferably slide radially inward and radially outward, for instance relative to the axis of the body element. In the first state, one or more, preferably all of the engaging elements have a first state position. In the second state, one or more, preferably all of the engaging elements have a second state position.

In the first state position an engaging element may be radial inward compared with when in the second state position. In the first state position, an engaging element may be closer to the axis of the body element. In the first state position, two or more engaging elements may have a reduced separation when compared with their separation in the second state position. The reduced separation may be a minimum separation distance.

In the second state position an engaging element may be radial outward compared with when in the first state position. In the second state position, an engaging element may be further from the axis of the body element. In the second state position, two or more engaging elements may have an increased separation when compared with their separation in the first state position. The increased separation may exceed a threshold separation distance, with the threshold separation distance being greater than the separation of the parts of the surgical component that are engaged in the first state, in use.

Preferably in the transition from the first state towards the second state, an engaging element may move radially outward away from the position in the first state position. In the transition from the first state towards the second state, an engaging element may move further from the axis of the body element. Preferably in the transition from the first state towards the second state, two or more engaging elements may have their separation increased when compared with their separation in the first state position. The increased separation may exceed a threshold separation distance, with the threshold separation distance being greater than the separation of the parts of the surgical component that are engaged in the first state, in use.

Preferably in the transition from the second state towards the first state, an engaging element may move radially inward away from the position in the second state position. In the transition from the second state towards the first state, an engaging element may move closer to the axis of the body element. Preferably in the transition from the second state towards the first state, two or more engaging elements may have their separation decreased when compared with their separation in the second state position. The decreased separation may be to within a separation distance range, with the separation distance range providing opposing contact with parts of the surgical component that are engaged in the first state, in use.

One or more or all of the engaging elements may be acted on by a biasing element. The biasing element may bias an engaging element towards the first state position for the engaging element. The biasing element may resist an engaging element moving from the first state position towards a second state position. The biasing element may be connected to the engaging element. The biasing element may be mounted on the support element. The biasing element may be a spring or a deformable component. The biasing element may be deformed during transition from the first state towards the second state.

For one or more or all of the engaging elements, the slidable mounting of the engaging element relative to the support element may be provided by: a recess to provide a mount; an elongate slot to provide a second mount; a connector engaged with the mount and the second mount. The recess may be a through aperture. The connector may be a bar or pin. The elongate slot may be a recess, but is preferably a through aperture. Preferably the connector passes through the mount and through the second mount. Preferably the mount is provided on an engaging element or on a part connected thereto. Preferably each engaging element is provided with a mount. Preferably the second mount is provided by the support element, for instance a rib extending from the support element. Preferably a second mount is provided for each engaging element.

The elongate slot may inclined. The elongate slot may have a distal end and a proximal end. The distal end of the elongate slot may be at a greater radial distance than the proximal end. The proximal end may have a lower radial distance than the distal end. The radial distance may be considered relative to the longitudinal axis of the body element. The radial distance may be considered relative to a location equidistant from the engaging elements and particularly the threaded surfaces thereof. The elongate slot may provide a ramp leading away from the body element and/or, in use, the surgical component. The ramp may lead up towards the distal end.

With the surgical component connecting device in a first state and with the surgical component connecting device connected to a surgical component, the surgical component connecting device may be considered to be in an engaged state. The connecting device may transition from the first state to the second state to transition from an engaged state to a released state. The surgical component and the connecting device may be moved relative to one another in the released state, for instance to remove the connecting device from the surgical component.

The surgical component connecting device transitioning from the first state towards the second state may include moving the support element away from the distal end of the connecting device. The surgical component connecting device transitioning from the first state towards the second state may include moving the elongate slot away from the distal end of the connecting device. The surgical component connecting device transitioning from the first state towards the second state may include outward radial movement of the connector. The surgical component connecting device transitioning from the first state towards the second state may include outward radial movement of the engaging elements. The surgical component connecting device transitioning from the first state towards the second state may include movement of the engaging elements out of contact with the surgical component, preferably outward radial movement.

The surgical component connecting device transitioning from the second state to the first state may include moving the support element towards the distal end of the connecting device. The surgical component connecting device transitioning from the second state to the first state may include moving the elongate slot toward the distal end of the connecting device. The surgical component connecting device transitioning from the second state to the first state may include inward radial movement of the connector. The surgical component connecting device transitioning from the second state to the first state may include inward radial movement of the engaging elements.

With the surgical component connecting device in the first state, the surgical component connecting device and the surgical component may be transitioned from a released state to an engaged state. The transition may include bringing the engaging elements of the connecting device into proximity with an engagement part of the surgical component. The transition may include rotating the connecting device relative to the surgical component. The transition may include engaging a threaded part of the surgical component with threaded sections of the engaging elements. The transition may bring a part of the surgical component into abutment with a distal face of the body element and/or support element.

The body element and/or support element may be provided within an outer cover. The outer cover may extend from the distal end towards the proximal end of the connection device. The outer body may provide the outer cover.

An operating element may be provided at or towards the proximal end of the connection device. The operating element may be operably connected to the support element, preferably so as to cause movement of the support element. The operating element may be rotatably mounted on the body element. Rotation in a first direction may cause slidable movement of the support element towards the distal end. Rotation in a second direction may cause slidable movement of the support element towards the proximal end. The operating element may be accessible through a gap or opening in the outer cover.

The first aspect of the disclosure may include any of the features, options or possibilities set out elsewhere in this document, including in the other aspects of the disclosure.

According to a second aspect of the disclosure, there is provided a kit comprising:
 one or more surgical components;
 a surgical component connecting device, the connecting device comprising:
  an outer body
  a body element;
  a support element, the supporting element being slidably mounted relative to the body element; and
  two or more surgical component engaging elements provided towards the distal end of the body element, at least one of the surgical component engaging elements being operably connected to the support element;
 wherein the two or more surgical component engaging elements have a first state and a second state, wherein the separation of the two or more surgical component engaging elements is greater in the second state than in the first state.

The one or more surgical components may be a surgical instrument. The surgical instrument may be one or more of a reamer [including acetabular reamers], a broach or a rasp, potentially of different configurations, such as different sizes. The surgical instrument may be a cutting block, potentially two or more cutting blocks of different configurations. The one or more surgical components may be a surgical implant or part thereof. The one or more surgical components may be a surgical fixing.

The surgical component connecting device may be provided with any of the features, options or possibilities set out elsewhere in this document, including in the first aspect of the disclosure.

The second aspect of the disclosure may include any of the features, options or possibilities set out elsewhere in this document, including in the other aspects of the disclosure.

According to a third aspect of the disclosure, there is provided a method of disconnecting a surgical component from a surgical component connection device, the method including:
 providing the surgical component;
 providing the surgical component connection device, the surgical component connecting device comprising:
  an outer body;
  a body element;
  a support element, the support element being slidably mounted relative to the body element;
  two or more surgical component engaging elements provided towards the distal end of the body element, at least one of the surgical component engaging elements being operably connected to the support element;
 wherein the two or more surgical component engaging elements have a first state and a second state, wherein the separation of the two or more surgical component engaging elements is greater in the second state than in the first state;
 providing the surgical component and the surgical component connection device in an engaged state, wherein the surgical component engaging elements are engaged with the surgical component and are in the first state;
 transitioning the surgical component engaging elements from the first state to a second state; and
 removing the surgical connection device from the surgical component to provide the disconnecting.

Preferably in the transition from the first state towards the second state, an engaging element may move radially outward away from the position in the first state position. In the transition from the first state towards the second state, an engaging element may move further from the axis of the body element. Preferably in the transition from the first state towards the second state, two or more engaging elements may have their separation increased when compared with their separation in the first state position. The increased separation may exceed a threshold separation distance, with the threshold separation distance being greater than the separation of the parts of the surgical component that are engaged in the first state, in use.

With the surgical component connecting device in a first state and with the surgical component connecting device connected to a surgical component, the surgical component connecting device may be considered to be in an engaged state. The connecting device may transition from the first state to the second state to transition from an engaged state to a released state. The surgical component and the connecting device may be moved relative to one another in the released state, for instance to remove the connecting device from the surgical component.

The surgical component connecting device transitioning from the first state towards the second state may include moving the support element away from the distal end of the connecting device. The surgical component connecting device transitioning from the first state towards the second state may include moving the elongate slot away from the distal end of the connecting device. The surgical component connecting device transitioning from the first state towards the second state may include outward radial movement of the connector. The surgical component connecting device transitioning from the first state towards the second state may include outward radial movement of the engaging elements. The surgical component connecting device transitioning from the first state towards the second state may include movement of the engaging elements out of contact with the surgical component, preferably outward radial movement.

The third aspect of the disclosure may include any of the features, options or possibilities set out elsewhere in this document, including in the other aspects of the disclosure.

According to a fourth aspect of the disclosure, there is provided a method of connecting a surgical component to a surgical component connection device, the method including:
  providing the surgical component;
  providing the surgical component connection device, the surgical component connecting device comprising:
    an outer body;
    a body element;
    a support element, the support element being slidably mounted relative to the body element;
    two or more surgical component engaging elements provided towards the distal end of the body element, at least one of the surgical component engaging elements being operably connected to the support element;
  wherein the two or more surgical component engaging elements have a first state and a second state, wherein the separation of the two or more surgical component engaging elements is greater in the second state than in the first state;
    providing the surgical component connection device with the surgical component engaging elements in the first state;
    contacting the surgical component connection device with the surgical component;
    transitioning the surgical component connection device and surgical component from a released state to an engaged state wherein the surgical component engaging elements are engaged with the surgical component.

With the surgical component connecting device in the first state, the surgical component connecting device and the surgical component may be transitioned from a released state to an engaged state. The transition may include bringing the engaging elements of the connecting device into proximity with an engagement part of the surgical component. The transition may include rotating the connecting device relative to the surgical component. The transition may include engaging a threaded part of the surgical component with threaded sections of the engaging elements. The transition may bring a part of the surgical component into abutment with a distal face of the body element and/or support element.

The surgical component engaging elements may be provided in the first state by a transition from the second state to the first state. This transition may provide that an engaging element may move radially inward away from the position in the second state position. This transition may provide that an engaging element may move closer to the axis of the body element. This transition may provide that two or more engaging elements may have their separation decreased when compared with their separation in the second state position. The decreased separation may be to within a separation distance range, with the separation distance range providing opposing contact with parts of the surgical component that are engaged in the first state, in use.

The surgical component connecting device transitioning from the second state to the first state may include moving the support element towards the distal end of the connecting device. The surgical component connecting device transitioning from the second state to the first state may include moving the elongate slot toward the distal end of the connecting device. The surgical component connecting device transitioning from the second state to the first state may include inward radial movement of the connector. The surgical component connecting device transitioning from the second state to the first state may include inward radial movement of the engaging elements.

The fourth aspect of the disclosure may include any of the features, options or possibilities set out elsewhere in this document, including in the other aspects of the disclosure.

BRIEF DESCRIPTION OF THE DRAWINGS

Various embodiments of the disclosure will now be described, by way of example only and with reference to the accompanying drawings in which:

FIGS. 4a and 4b are exploded perspective views of a further embodiment of the handle element.

DETAILED DESCRIPTION OF THE DRAWINGS

In surgery, such as orthopaedic surgery, there are a large number of situations in which two components need to be connected together. The connection mechanism used must be robust and yet easily operated. Male and female thread combinations, such as nut and bolt combinations, are very frequently used in such situations.

A potential issue with the nut and bolt approach is the time taken to connect two threaded components together and the time taken to release those two components once the connection is no longer required.

The surgical component may be a tool or instrument. The surgical component may be an implant or part thereof. The surgical component may be a fixing. The present disclosure is particularly suitable for use with reamers, broaches or rasps and similar surgical instruments. The present disclosure is also particularly suitable for use with cutting blocks and the like.

The present disclosure is beneficial in providing a strong axial lock for the components, whilst coupling the two for effective rotation together, such as a reamer and a shaft. The threaded engagement also pulls any slack out of the connection and so creates a very strong attachment for the components which improves accuracy. This is possible with a small sized component suitable for many applications. The speed with which the two components can be disconnected using the disclosure is also beneficial.

Figure 1:
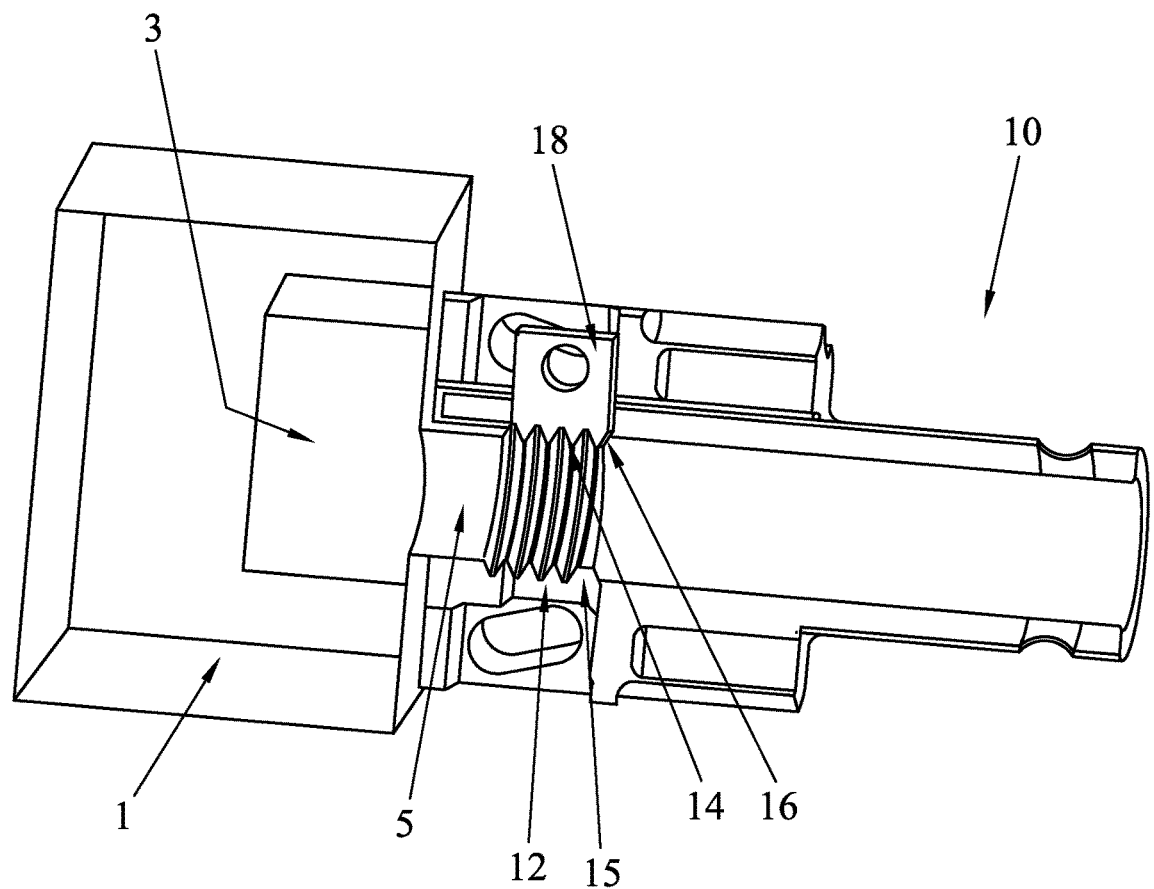
FIG. 1 is a cross-sectional side view of a handle element according to the disclosure, engaged with a threaded component.

In FIG. 1, a surgical component 1, in an orthopaedic surgery context, is provided with a stem 3 carrying a male thread 5. In this case a 6 mm thread is being used, but the disclosure can accommodate different thread pitches as necessary.

The component 1 is shown connected to a connecting device 10, provided according to the disclosure. The part of component 1 shown is representative of a part of any of the different surgical components possible, thus the component 1 may be a tool or instrument, a surgical implant, a surgical fixing or an intermediate component [such as an adaptor] provided between the distal component and the connecting device 10.

In FIG. 1, a first state for the connecting device 10 is shown. In this first state, the connecting device 10 is connected to the component 1 via a threaded engagement. The threaded engagement is formed by the interaction of the thread 5 of the component 1 with the thread 12 provided on the connecting device 10. In the illustrative embodiment, the thread 12 has two sections. A first section 14 of the thread 12 is provided on the inner surface 16 of a first surgical component engaging element, which is identified as a first sliding element 18. In opposition to this is a mirror image second surgical component engaging element [not shown] and having a second section 15 of the thread 12 on its inner surface. The first part 14 and the second part being in opposition forms a full and complete threaded engagement offering the robust connection levels desired of the arrangement. The first sliding element 18 and the second sliding element correspond in this embodiment in terms of their features, operation and interrelationship with other elements. Instead of the first sliding element 18 and the second sliding element in direct opposition with one another, it would be possible to space, evenly or unevenly, sliding elements around the perimeter of the connecting device, provided there was some extent of opposing abutment/engagement with the component 1.

Figure 2A:
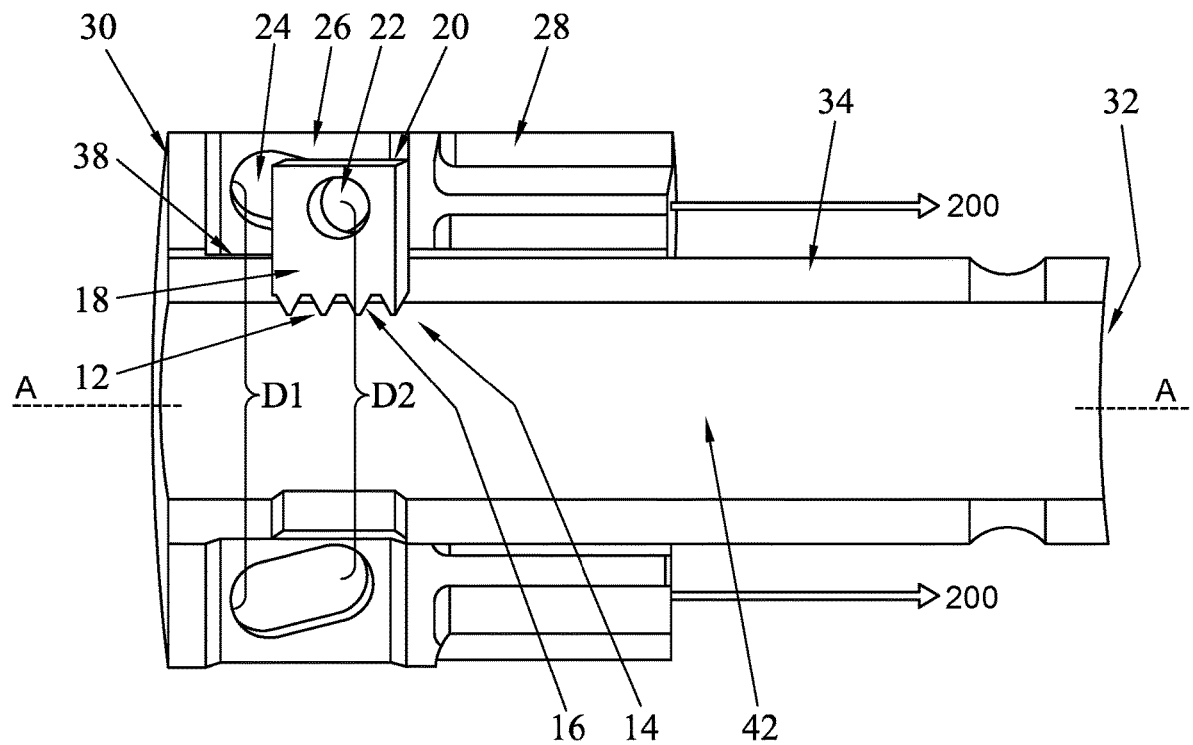
FIG. 2a is an illustration of the handle element in a first state, with the handle element adapted to engage a threaded component.

Referring to FIG. 2a, the first sliding element 18 and hence its inner surface 16 and the first part 14 of the thread 12 are held in position, in the first state, as follows. The first sliding element 18 extends radially from the inner surface 16 to an outer surface 20. Between the inner surface 16 and the outer surface 20, a mount, exemplified by an aperture 22 through the first sliding element 18 is provided. The aperture 22 receives a connector, exemplified by pin 400, shown in FIG. 4. The pin 400 also passes through a second mount, exemplified by an elongate slot 24 provided on a rib 26 depending from a support element, exemplified here as an external ring element 28. The elongate slot 24 is inclined relative to the central axis A-A of the connecting device 10. The slot 24 is at a greater diametric distance D1 closer towards the distal end 30 of the connecting device 10 and a lesser diametric distance D2 further from the distal end 30 and towards the proximal end 32 of the connecting device 10. In effect, the slot 24 provides a ramp away from the axis A-A towards the distal end 30 of the connecting device 10. In the first state, the pin is at the lesser radial distance D2.

The external ring element 28 is mounted on the outside of a body element, exemplified here by a shaft 34, in a slidable manner. The external ring element 28 is capable of axial movement relative to the shaft 34, but with the axial position of the shaft 34 fixed [see the difference in position in FIGS. 2a and 2b]. The shaft 34 is provided with a shaft slot 38 that extends through the wall thickness of the shaft 34. The shaft slot 38 also extends along a length of the shaft 34. The rib 26 provided on the external ring element 28 depends inward therefrom and is provided to one side of the shaft slot 38, such that the adjacent first sliding element 18 is able to extend radially inward into a bore 42 extending along the axis A-A of the connecting device 10. This presents the first part 14 of the thread 12 to the thread 5 of the component 1 when that is present in the bore 42. An opposing, but equivalent structure is provided for the second sliding element [not shown].

Figure 2B:
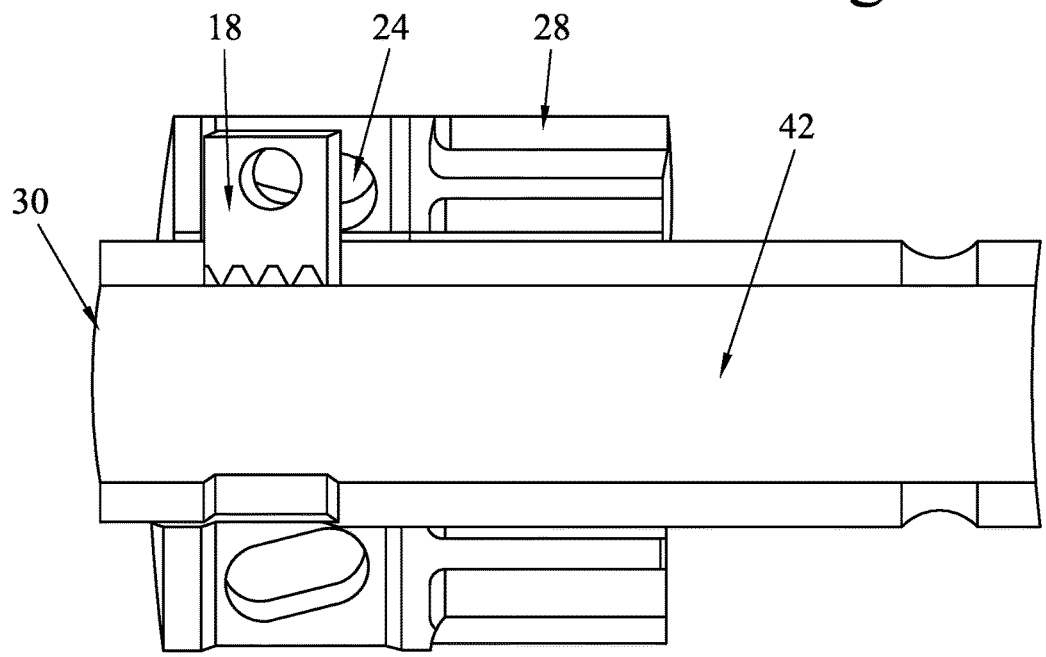
FIG. 2b is an illustration of the handle element of FIG. 2b, with the handle element in a second state, released from any engagement.

A spring 402, shown in FIG. 4, is provided to urge axially the external ring element 28 towards the distal end 30 of the shaft 34 [the FIG. 2a position] and to resist movement axially of the external ring element 28 towards the proximal end 32 of the shaft 34 [the FIG. 2b position].

When the user desires to disconnect the connecting device 10 from the component 1, the connecting device 10 is transitioned from the first state to a second state; the second state providing a released state. The second state is shown in FIG. 2b.

During the transition, the external ring element 28 is slid away from the distal end 30 of the connecting device 10 and towards the proximal end [not shown] of the connecting device 10 as indicated by arrows 200 in FIG. 2a. The sliding motion causes the elongate slot 24 to move axially and the inclination of the slot 24 causes outward radial movement of the pins 400 and hence of the first sliding element 18 and the second sliding element. This radial movement out and away from the central bore 42 removes the sections of thread 12 from engagement with the thread 5 on the component 1. The elongate slot 24 is configured such that the movement of the sections of female thread 12 are sufficient radially so as to provide no interference with axial relative movement of the component 1 and connecting device 10 remain. A very fast, easily operated and reliable transition from the first state to the second state is provided to give the desired release.

The annular extent of the shaft slot 38 is only slightly greater than the thickness of the first sliding element 18 and so the sides of the shaft slot 38 lock the external ring element 28 in a fixed angular position relative to the shaft 34. Sliding movement is possible, but not rotation.

To transition from the second state to the first state, the external ring element 28 is slide towards the distal end of the shaft 34 and so causes the inward radial movement of the first sliding element 18 and second sliding element, together with their sections of female thread 12. Rotation of the shaft 34 then causes rotation of the first and second sliding elements and the sections of thread 12 and so causes and increases engagement with the male thread 5 on the stem 3 to provide the engagement.

In an embodiment of the disclosure, not shown, the inward radial movement of the first sliding element 18 and the second sliding element to the first state positions and/or the maintenance of those first state positions may be assisted by one or more biasing elements. These may be mounted on the external ring element and act on the sliding elements. The biasing element may be a spring or a deformable component. The biasing element may be deformed during transition from the first state to the second state and so may promote the return of the sliding elements to the first state positions.

As a consequence, the disclosure provides a reliable connection mechanism, which offers the robust and reliable connection of a threaded system, but at the same time is far faster to disengage. The nut element can be very rapidly released and then axially disengaged.

Figure 3:
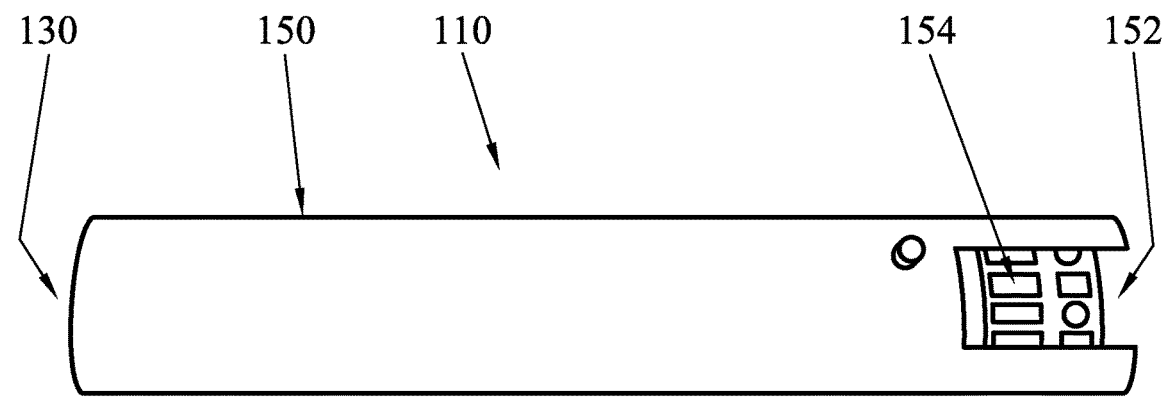
FIG. 3 is a perspective view of a prototype handle element according to the disclosure.

FIG. 3 provides an illustration of a connecting device 110 embodying the present disclosure. The distal end 130 of the connecting device 110 provides the central bore 42 and fastening mechanism in the manner described above. The external ring element 28 is provided within an outer housing 150 to provide clean lines for the device and contain the mechanism. The proximal end 152 of the connecting device 110 is provided with a rotatable element 154 which, on rotation in a first direction, causes rotation of the external ring element 28, the rib 26, first sliding element 18 and second sliding element, together with the sections of thread 12 and hence the engagement between the connecting device 10 and the component 1. A spring 402 urges the external ring element 28 to remain at the distal end 130 and so maintains the first sliding element 18 and second sliding element in the first state.

Pulling back on the external ring element 28, against the spring 402, causes the external ring element 28 to move towards the proximal end 152 of the connecting device 110 and so moves the pins 400 axially and hence the first sliding element 18 and the second sliding element outward radially and hence causes the transition to the second, released state. The connecting device 110 can then be axially retracted off the component 1.

FIG. 4*a* and FIG. 4*b* provide an exploded view of a similar connecting device 210, together with a surgical component 201 and stem 203. In this case, the outer housing 250 provides the same clean lines for the for the device and allows the user to hold the device. The rotatable element 254 is provided at the distal end 230 and includes the external ring element 228, the rib 226, providing the mounting for the first sliding element 218 by way of pin 500. The second sliding element 502 is also present together with the pin 504 used to mount it too. The sections of thread 212, the provide the engagement between the connecting device 210 and the component 201, are visible. A spring 402 urges the external ring element 228 to remain at the distal end 230 and so maintains the first sliding element 218 and second sliding element 502 in the first state.

Pulling back on the external ring element 228, against the spring 402, causes the external ring element 228 to move towards the proximal end 252 of the connecting device 210 and so moves the pins 500, 504 axially and hence the first sliding element 218 and the second sliding element 502 outward radially and hence causes the transition to the second, released state. The connecting device 210 can then be axially retracted off the component 201.

The invention claimed is:

1. A surgical component connecting device, the connecting device comprising:
   an outer body;
   a body element;
   a support element, the support element being slidably mounted relative to the body element; and
   two or more surgical component engaging elements provided towards a distal end of the body element, at least one of the surgical component engaging elements being operably connected to the support element;
   wherein the two or more surgical component engaging elements have a separation distance in a first state and a second state, wherein the separation distance of the two or more surgical component engaging elements is greater in the second state than in the first state, and
   wherein one or more of the engaging elements are slidably mounted relative to the support element by:
   a recess to provide a mount,
   an elongate slot to provide a second mount, and
   a connector engaged with the mount and the second mount.

2. A device according to claim 1, wherein the body element is rotatably mounted relative to the outer body.

3. A device according to claim 1, wherein the two or more surgical component engaging elements are slidably mounted relative to the support element, the two or more surgical component engaging elements sliding radially inward and radially outward relative to an axis of the device.

4. A device according to claim 1, wherein, in the first state the two or more surgical component engaging elements have a first state position and in the second state the two or more surgical component engaging elements have a second state position, wherein in the first state position at least one of the two or more surgical component engaging elements is radially inward relative to an axis of the device compared with when in the second state position, and wherein, in the first state position, the two or more surgical component engaging elements have a reduced separation when compared with their separation in the second state position.

5. A device according to claim 1, wherein, in the first state the two or more surgical component engaging elements have a first state position and in the second state the two or more surgical component engaging elements have a second state position, wherein in the second state position at least one of the two or more surgical component engaging elements is radially outward relative to an axis of the device compared with when in the first state position, and wherein in the second state position, the two or more surgical component engaging elements have an increased separation when compared with their separation in the first state position.

6. A device according to claim 1, wherein the elongate slot for each surgical component engaging element is inclined, each elongate slot having a distal end and a proximal end, the distal end of each elongate slot being at a greater radial distance from an axis of the device than the proximal end of the elongate slot.

7. A device according to claim 1, wherein the elongate slot provides a ramp leading away from the body element, the ramp leading up towards a distal end of the device.

8. A device according to claim 1, wherein each mount is provided on the two or more surgical component engaging elements or on a part connected thereto and the second mount is provided by the support element on a rib extending from the support element.

9. A device according to claim 1, wherein, in the first state the support element is closer to a distal end of the body element than in the second state.

10. A device according to claim 1, wherein the support element is restrained from rotation relative to the body element.

11. A device according to claim 1, wherein the two or more surgical component engaging elements oppose one another.

12. A device according to claim 1, wherein the two or more surgical component engaging elements are acted on by a biasing element, the biasing element biasing each surgical component engaging element towards the first state.

13. A device according to claim 1, wherein an operating element is provided at or towards a proximal end of the device, the operating element being operably connected to the support element to cause movement of the support element.

14. A device according to claim 13, wherein the operating element is rotatably mounted on the body element, rotation in a first direction causing slidable movement of the support element towards a distal end of the device and rotation in a second direction causing slidable movement of the support element towards the proximal end of the device.

15. A device according to claim 1, wherein the body element has a proximal end and a distal end, the distal end of the body element providing a connection location for a surgical component, the body element being provided with a bore at its distal end, the connection location being provided within the bore.

16. A surgical component connecting device, the connecting device comprising:
an outer body;
a body element;
a support element, the support element being slidably mounted relative to the body element; and
a plurality of surgical component engaging elements provided towards a distal end of the body element, each surgical component engaging element including an engaging element body being operably connected to the support element and a plurality of teeth defined on the engaging element body that are configured to engage a surgical component and;
wherein the teeth of the plurality of surgical component engaging elements have a separation distance in a first state and a second state, wherein the separation distance of the two or more surgical component engaging elements is greater in the second state than in the first state, and
wherein each engaging element is slidably mounted relative to the support element by:
a recess defined in the engaging element body to provide a mount,
an elongate slot to provide a second mount, and
a connector engaged with the mount and the second mount.

17. A device according to claim 16, wherein the engaging elements are acted on by a spring, the spring biasing an engaging element towards the first state for the engaging element.

18. A device according to claim 16, wherein the elongate slot for each surgical component engaging element is inclined, each elongate slot having a distal end and a proximal end, the distal end of each elongate slot being at a greater radial distance from an axis of the device than the proximal end of the elongate slot.

19. A device according to claim 16, wherein the elongate slot provides a ramp leading away from the body element, the ramp leading up towards a distal end of the device.

20. A surgical component connecting device, the connecting device comprising:
an outer body;
a body element;
a support element, the support element being slidably mounted relative to the body element; and
two or more surgical component engaging elements provided towards a distal end of the body element, at least one of the surgical component engaging elements being operably connected to the support element;
wherein the two or more surgical component engaging elements have a separation distance in a first state and a second state, wherein the separation distance of the two or more surgical component engaging elements is greater in the second state than in the first state, and
wherein each of the two or more surgical component engaging elements are provided with a surgical component engaging surface, each engaging surface being provided with a threaded portion facing inward towards a longitudinal axis of the surgical component connected device.

* * * * *